United States Patent [19]

Hervé et al.

[11] Patent Number: 4,492,687
[45] Date of Patent: Jan. 8, 1985

[54] LIGHT-STABLE PESTICIDAL COMPOSITIONS

[75] Inventors: Jean-Jacques Hervé, Aubagne; Jean-Claude Suglia, Le Destrousse; Colette Meinard, Marseille, all of France

[73] Assignee: Roussel Uclaf, Paris, France

[21] Appl. No.: 550,082

[22] Filed: Nov. 8, 1983

Related U.S. Application Data

[62] Division of Ser. No. 271,989, Jun. 9, 1981, Pat. No. 4,440,756.

[30] Foreign Application Priority Data

Jun. 11, 1980 [FR] France .................. 80 12960
Jan. 16, 1981 [FR] France .................. 81-00752

[51] Int. Cl.³ ............................................. A01N 25/22
[52] U.S. Cl. ................................................. 424/174
[58] Field of Search ...................................... 424/174

[56] References Cited

U.S. PATENT DOCUMENTS

| | | | |
|---|---|---|---|
| 2,772,198 | 11/1956 | Smith et al. | 424/188 |
| 3,936,419 | 2/1976 | Wang et al. | 424/174 |
| 3,943,239 | 3/1976 | Yamaguchi et al. | 424/174 |
| 3,981,884 | 9/1976 | Wang et al. | 424/174 |
| 4,171,355 | 10/1979 | Stubbs et al. | 424/174 |
| 4,224,227 | 9/1980 | Martel et al. | 424/274 |
| 4,310,542 | 1/1982 | Martel et al. | 424/189 |
| 4,341,760 | 7/1982 | Matthewson | 424/45 |

OTHER PUBLICATIONS

CA 77/170800t Liquid Filters for the Ultraviolet, Visible, and near Infrared, Ingersoll, K. A. (Bell Teleph. Lab., Inc., Murray Hill, N.J.) Appl. Opt. 1972, 11(11), 2473-2476.

CA 78/59 778y Light Resistant Red Dye, Moskvitin, N. I.; Kadykov, V. V. USSR 355 200, Oct. 16, 1972. From Otkrytiya, Izobret., Prom. Obraztsy, Tovarnye Znaki 1972, 49(31), 85.

*Primary Examiner*—Stanley J. Friedman
*Assistant Examiner*—John M. Kilcoyne
*Attorney, Agent, or Firm*—Charles A. Muserlian

[57] ABSTRACT

Novel light-stable pyrethrinoid pesticidal compositions comprising (a) at least one liquid vehicle, (b) at least one surface-active agent soluble in the said liquid vehicle, (c) at least one azodyestuff stabilizer and (d) at least one ester of the formula

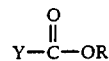

29 Claims, 10 Drawing Figures

LIGHT-STABLE PESTICIDAL COMPOSITIONS

PRIOR APPLICATION

This application is a division of our copending, co-pending, commonly assigned U.S. Pat. Application Ser. No. 271,989 filed June 9, 1981, now U.S. Pat. No. 4,440,756.

U.S. Pat. No. 2,772,198 and French Pat. No. 2,096,962 describe azodyestuff stabilizer for pyrethrinoids different from these of the present application.

U.S. Pat. No. 4,224,227 which is assigned to the assignee of the present application describes the compounds of formula I and their use as excellent agents for combatting pests such as insects, ticks, acariens, etc. However, it has been found that the said compounds are sensitive to light and may decompose when subjected to sunlight under use conditions.

OBJECTS OF THE INVENTION

It is an object of the invention to provide light-stable pesticidal compositions containing at least one compound of formula I as the active ingredient.

It is another object of the invention to provide an improved process for combatting pests.

These and other objects and advantages of the invention will become obvious from the following detailed description.

THE INVENTION

The novel light-stable pyrethrinoid compositions of the invention are comprised of (a) at least one liquid vehicle, (b) at least one surface-active agent soluble in the said liquid vehicle, (c) at least one azodyestuff stabilizer selected from the group consisting of a mixture of 1-[{4-(phenyl-azo)-phenyl)}-azo]-3-naphthalenol and 4-[{4-(phenylazo)-phenyl}azo]-phenol (a compound of Scarlet R), 1-[4-(4-phenylazophenyl)-azo]-naphthalene (Red organol BS), 1-[{2-methyl-4-(2-methylphenylazo)-phenyl}-azo]-2-naphthalenol (Red Sudan IV), 1-[(2-methoxyphenol)-azo]-2-naphthaphenol (Vermillion organol) 1-[(1-naphthalenyl)-azo]-2-naphthalenol (Scarlet 2R for fat), 1-(phenylazo)-2-naphthalenol (Sudan I), 1-[(2-hydroxy-4-methyl-phenyl)-azo]-2-naphthalenol (Sudan II), 1-[{dimethyl-4-[(dimethylphenyl)-azo}-phenylazo]-2-naphthalenol (Red to fat 5B), N-ethyl-1-[{4-(phenylazo)-phenyl}-azo]-2-naphthlenylamine (Red to fat 7B), 1-[{1-naphthalenyl}-azo]-2,4-benzenediamine (Brown RR to fat), 2-[(2-methoxyphenyl)-azo]-phehol (Red to fat G), disodium 4-hydroxy-3-[(4-sulfo-1-naphthalenyl)-azo]-1-naphthalene sulfonate (azo ruby), 4-[(4-ethoxyphenyl)-azo]-1-naphthalenol (Brown to fat B), 2,4-dihydro-5-methyl-2-phenyl-4-(phenylazo)-3H-pyrazol-3-one (Yellow to fat 3G), N,N-diethyl-4-(phenylazo)-benzeneamine (Yellow to fat GGN), 2,3-dihydro-2,2-dimethyl-6-[(4-phenylazo)-1-naphthalenyl]-azo-1H-perimidine (Black to fat HB), N-[4-phenyl)-(4-phenylamino)-1-naphthalenyl]-methylene-2,5-cyclohexadien-1-ylidene-N-methylmethaniminium chloride (Blue to fat B) and 1-/(4(phenylazo) phenyl)azo/ 2-naphtalenol and at least one ester of the formula wherein Y is selected from the group consisting of in its various stereoisomeric forms and mixtures thereof, Z is alkyl of 1 to 6 carbon atoms, Y is selected from the group consisiting of hydrogen, halogen, —CN, —NO$_3$, alkyl of 1 to 4 carbon atoms and alkoxy of 1 to 4 carbon atoms, n is 0, 1, 2 or 3, W is selected from the group consisting of $X_1$ is selected from the group consisting of hydrogen, fluorine, chlorine and bromine, $X_2$ is selected from the group consisting of fluorine, chlorine bromine, $X_3$ is selected from the group consisting of chlorine, bromine and iodine, $X_4$ is a halogen and $X_5$ is halogen optionally other than that of $X_4$ and due to asymetric carbon atom in W, the compounds are in the A isomer or B isomer form or mixtures thereof and R is selected from the group consisting of and benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy, benzyl and halogens, $R_1$ is selected from the group consisting of hydrogen and methyl, $R_2$ is selected from the group consisting of monocyclic aryl and —CH$_2$—C≡CH, $R_3$ is an aliphatic of 2 to 6 carbon atoms having at least one carbon-carbon insaturation, $R_4$ is selected from the group consisting of hydrogen, —CN, CH$_3$ and —C≡CH, $R_5$ is selected from the group consisting of chlorine and methyl, n is 0, 1 or 2, $R_6$, $R_7$, $R_8$ and $R_9$ are individually selected from the group consisting of hydrogen, chlorine and methyl and S/I indicates that the ring may be aromatic, dihydro or tetrahydro the alcoholic moiety R—OH being capable of containing one or more asymmetric carbon atoms and of existing in the form of various stereoisomers. The compositions are preferably in the form of an emulsifable concentrate.

Among the preferred light-stable compositions of the invention are those wherein the azodyestuff is a mixture of 1-[{4-(phenylazo)-phenyl}-azo]-3-naphthalenol and 4-[{4-(phenylazo)-phenyl}-azo]-phenol (Scarlet to fat), those wherein the azodye-stuff is 1-[{4-(phenylazo)-phenyl}-azo]-2-naphthalenol, those wherein the azodyestuff is N-ethyl-1-[{4-(phenylazo)-phenyl}-azo]-2-naphthalenylamine (or Red to fat 7B) and those wherein the azodyestuff is N,N-diethyl-4-(phenylazo)-benzeneamine (Yellow to fat GGN).

Among the preferred light-stable compositions of the invention are compositions containing compounds of formula I wherein R is and especially α-cyano-3-phenoxy-benzyl or α-ethynyl-3-phenoxy-benzyl or 3-phenoxy-benzyl.

The most preferred compositions of the invention are those containing as the active ingredient an ester selected from the group consisting of (S)α-cyano-3-phenoxy-benzyl (1R, cis) 2,2-dimethyl-3-(2,2-dibromovinyl)-cyclopropane-1-carboxylate, (S)α-cyano-3-phenoxy-benzyl (1R, cis) 2,2-dimethyl-3-(2,2-dichloro-1,2-dibromo-ethyl)-cyclopropane-1-carboxylate, (S)α-cyano-3-phenoxy-benzyl (1R, trans) 2,2-dimethyl-3-(2,2-dichloro-1,2-dibromo-ethyl)-cyclopropane-1-carboxylate and (S)α-cyano-3-phenoxy-benzyl (1R, cis)2,2-dimethyl-3-(1,2,2,2-tetrabromo-ethyl)-cyclopropane-1-carboxylate.

The compositions preferably contain 5 to 100 g per liter of at least one active compound of formula I and 0.1 to 10 g per liter of at least one azodyestuff stabilizer. The liquid vehicle may be of a wide variety of liquids and a preferred group of liquids are aromatic hydrocarbons such as xylene or toluene.

The surface active agents may also be of a wide variety. Examples of preferred surface active agents are members of the group consisting of polyoxyethylene polymethylsiloxane, polyethylenepolyoxypropylene polymethylsiloxane, monolaurate of sorbitol anhydrous oxyethylene, monooleate of sorbitol anhydrous oxyethylene, tridecylalcohol oxyethylene, nonylphenol oxyethylene, polyglycolic ethers of fatty alcohols, tributylphenylopolyglycolic ethers, calcium salts of alkylsulfonic acids and aryl sulfonic acids, phosphoric esters, alkylamino polycarboxylic acid derivatives, alkali metal salts of polyvalent amines, salts of organic carboxylic acids and organosulfonic acids, lignosulfonates, N-sulfo or N-phosphosuccinates of esters of α-amino acids, alkyl naphthalene sulfonates, condensation products of aminosulfonic acids or aminocarboxylic acids with alkyl haloacetic acids and polyglycerol oleates.

The degree of protection of the pyrethrinoids from light is evidentially not identical with all the surface active agents used in the case that all other factors are the same. It is especially noted that the association of the surface active agent with the azodyestuffs results in good protective results. Especially preferred surface active agents are phosphoric acid esters and polyglycerol oleates.

In a preferred modification of the invention, the compositions also contain a component capable of fixing the mixture of the invention to the vegetable leaves such as ethylcellulose.

The process of the invention for the stabilization of pesticidal compositions comprises incorporating into a mixture of at least one compound of formula I in at least one liquid vehicle an effective amount of at least one surface active agent soluble in the liquid vehicle and at least one of the azodye-stuffs recited above. Preferably, the compositions contain 5 to 100 g per liter of the pyrethrinoids of formula I and 0.1 to 10 g per liter of the azodyestuff stabilizer and 1 to 100 g/liter of surface active agent.

It is perceived that the emulsifiable concentrates containing the pyrethrinoids as the active ingredient see the latter being degraded by light in such a manner that practical use of these compositions can become impossible. Due to the stabilized compositions of the invention, compositions which are in the form of an emulsifiable concentrate and which contain azedyestuffs, diverse classes of pyrethrinoids enumerated above as formula I have increased stability as demonstrated in the examples infra.

The stabilized compositions of the invention are capable of being used in agriculture, especially in open fields without loss of activity and under the most economical conditions. The same compounds not stabilized with azodyestuffs are usually degraded to a such a large extent by the action of light so that their use is not economical. Due to the intense insecticidal activity of the pyrethrinoids of formula I, the invention assumes a great practical importance.

The method of the invention for combatting pests comprises contacting the pests with a pesticidal amount of a composition of the invention. The usual useful dose as an agricultural insecticide is 1 to 100 g per hectare.
Referring now to the FIGS.:

The FIGS. are graphs of the insecticidal activity of the examples and clearly show the very important stabilization to the light due to the use of the azodyestuffs.

Figure 1:
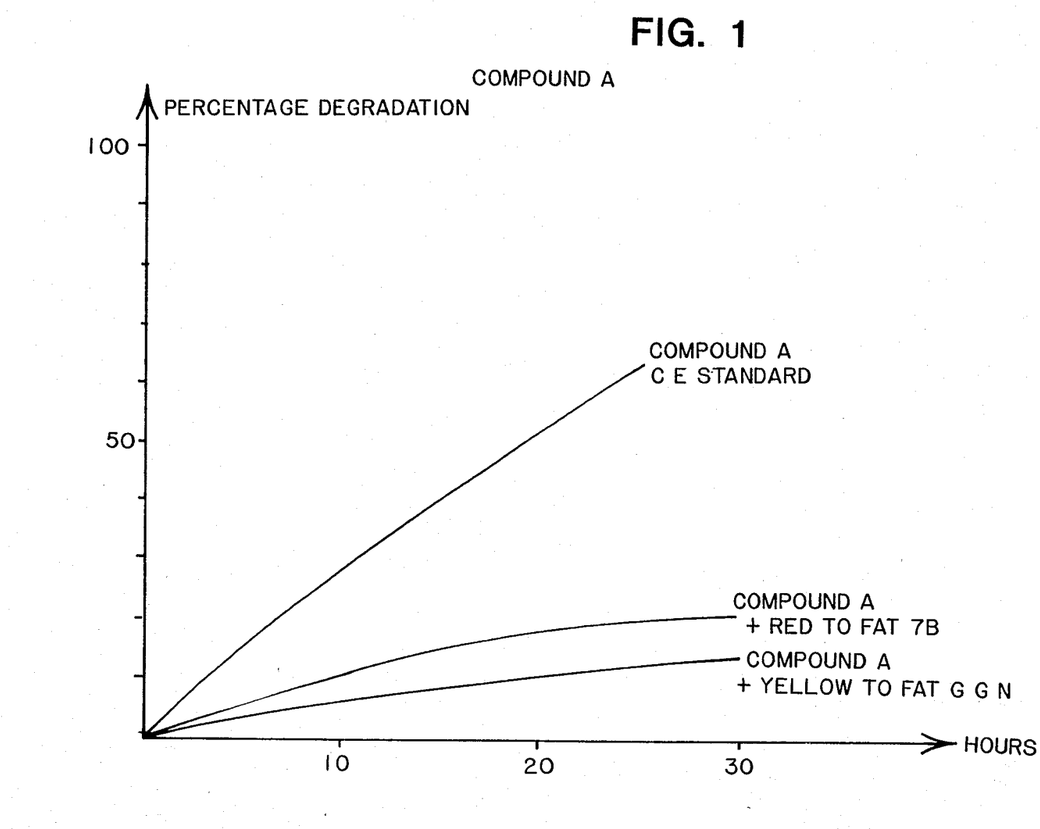
Figure 2:
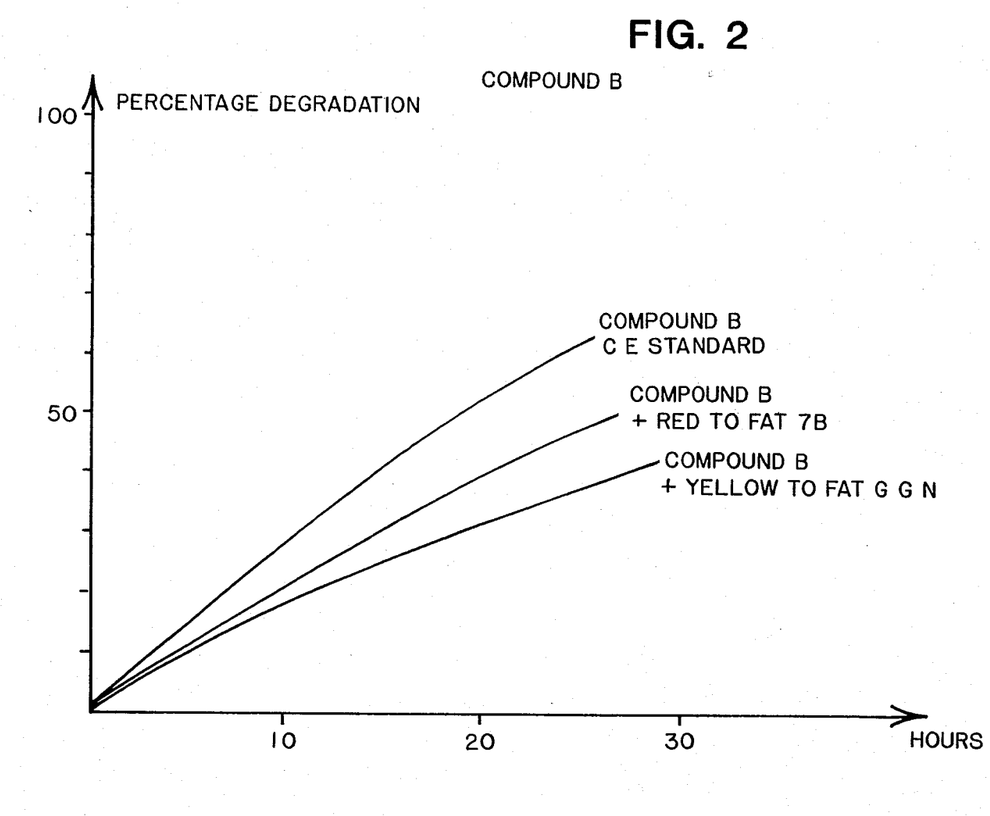
Figure 3:
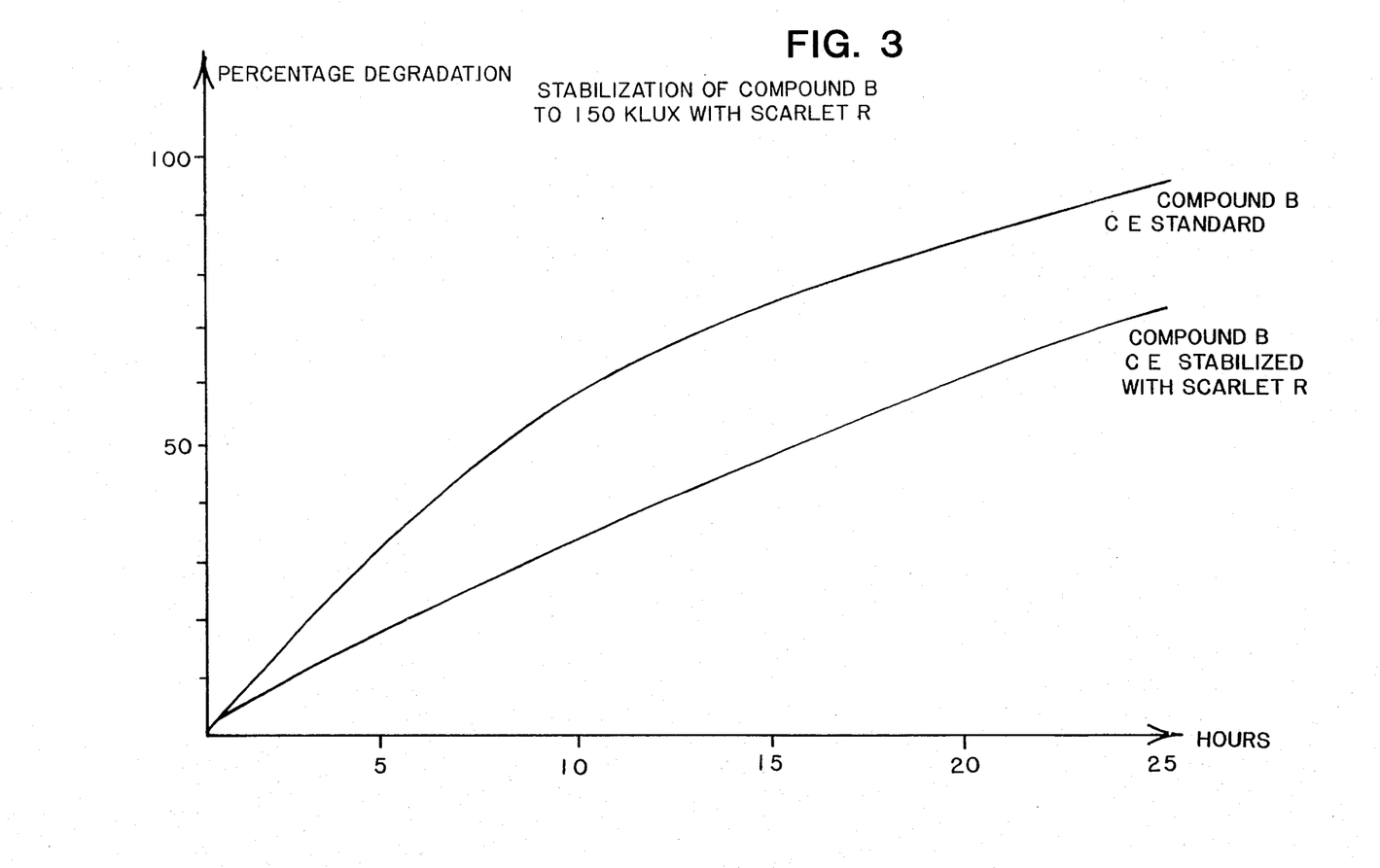
Figure 4:
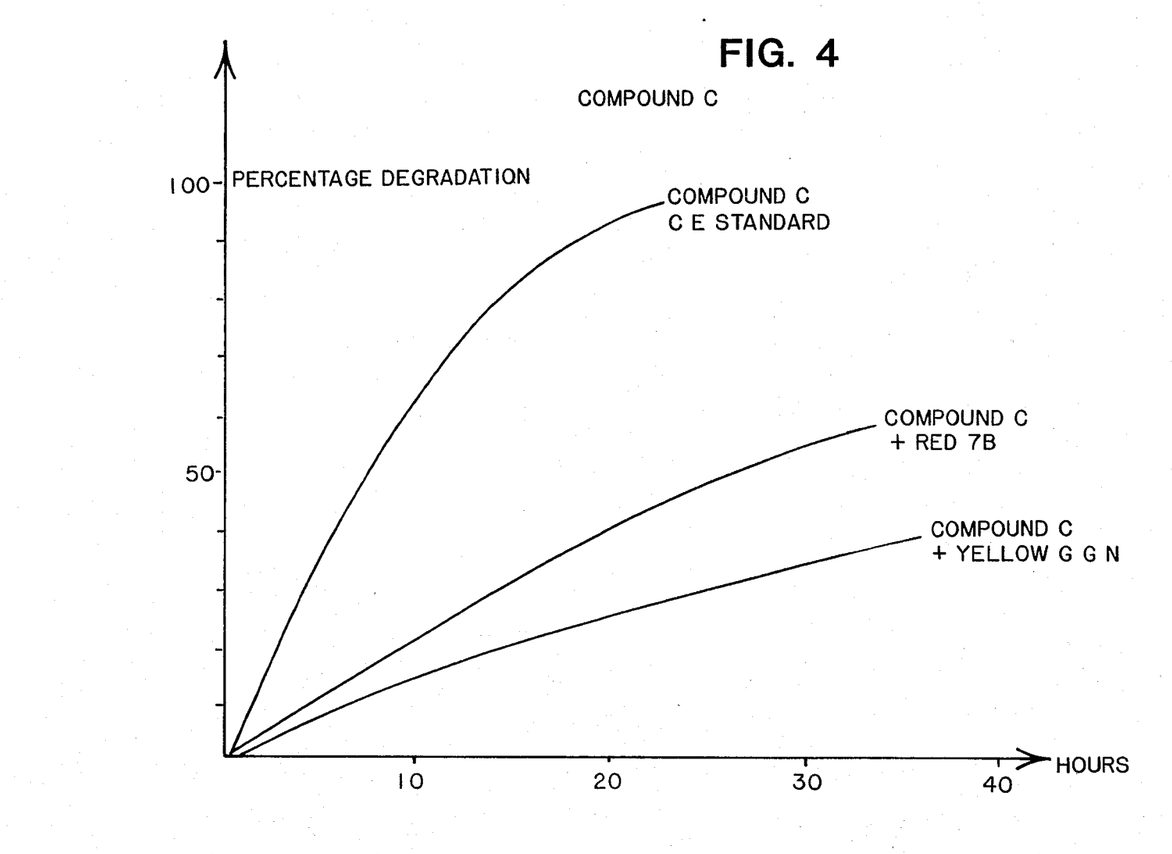
Figure 5:
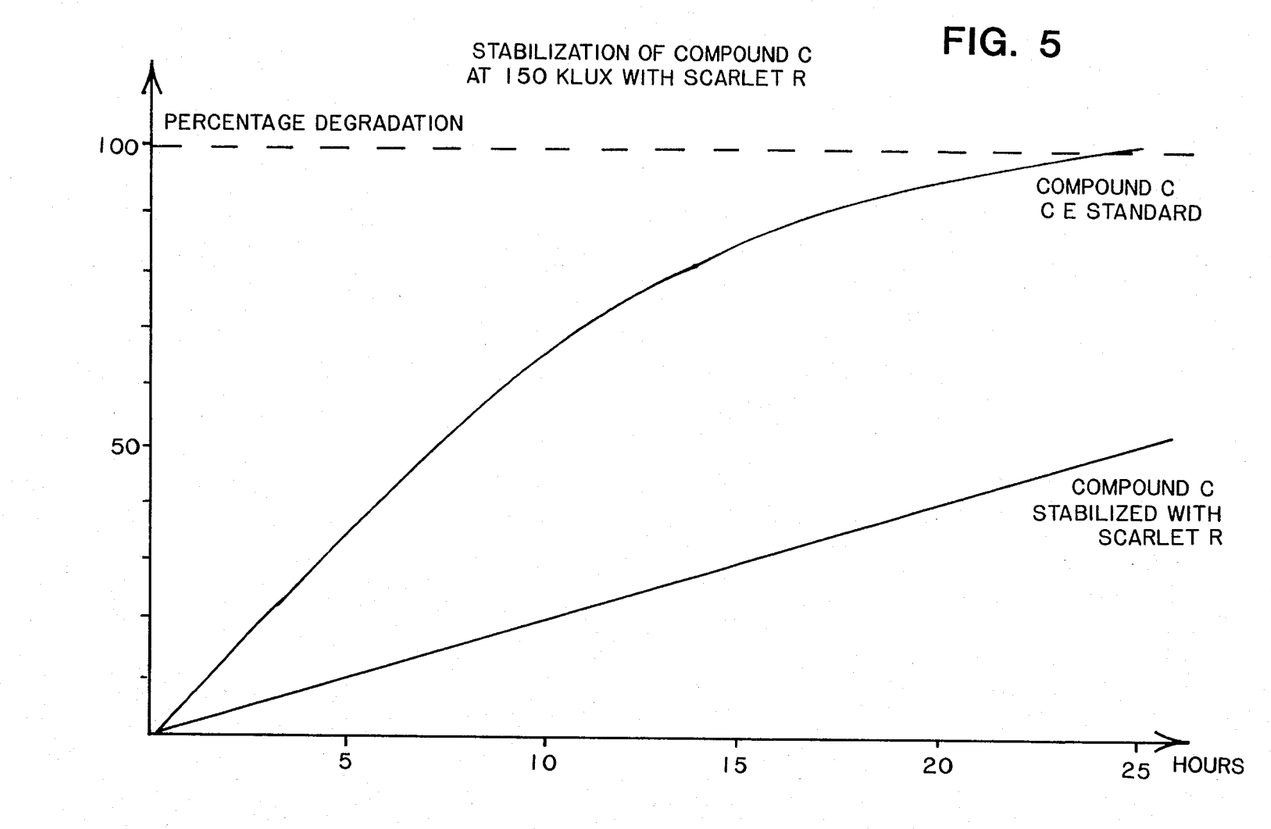
Figure 6:
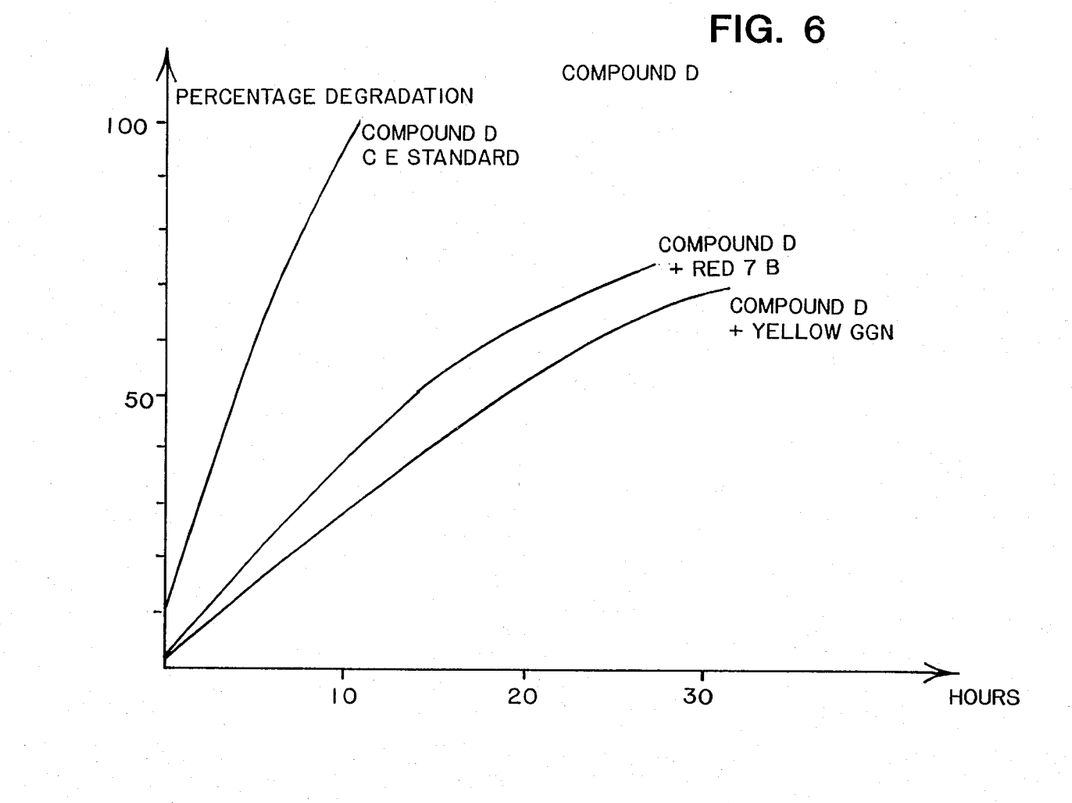
Figure 7:
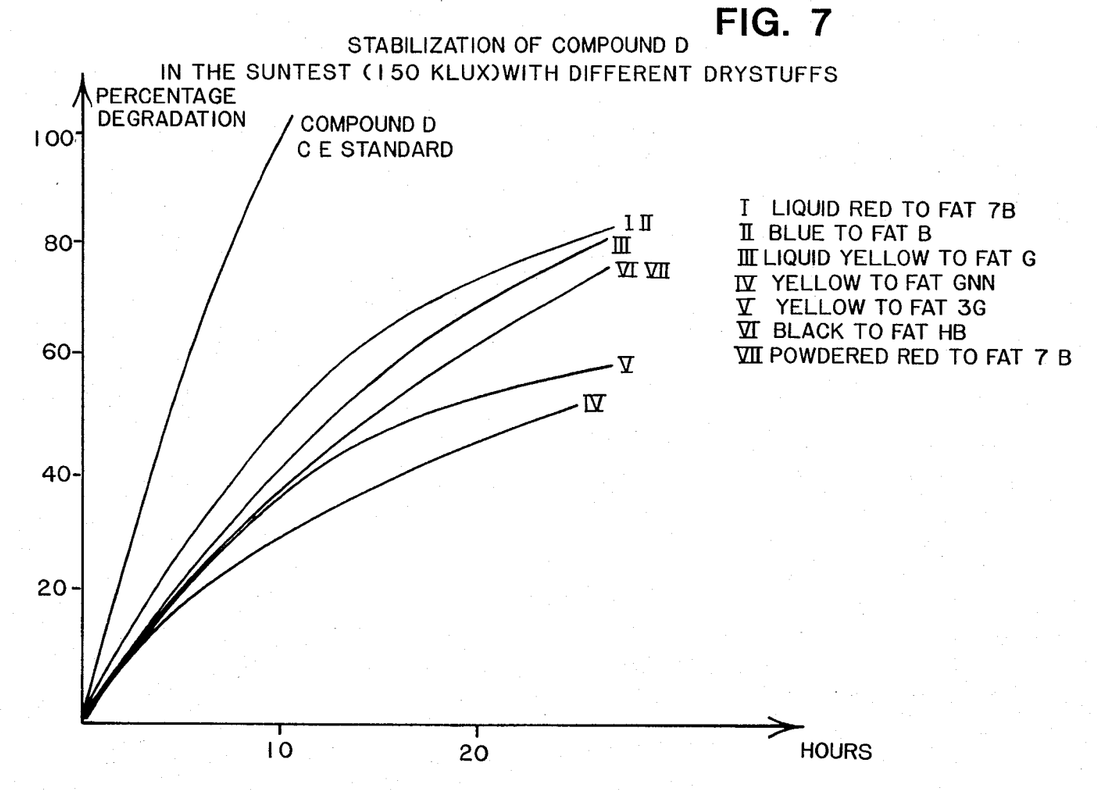
Figure 8:
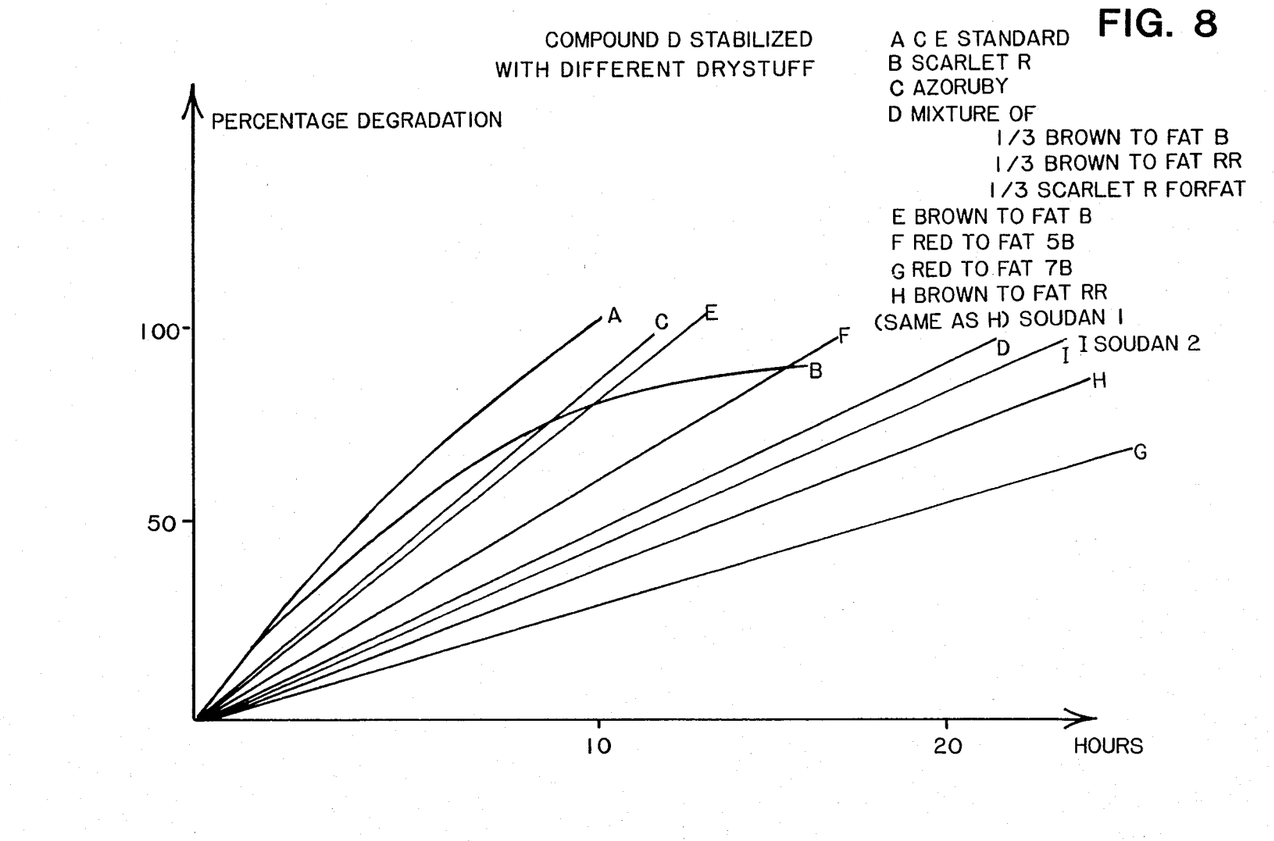
Figure 9:
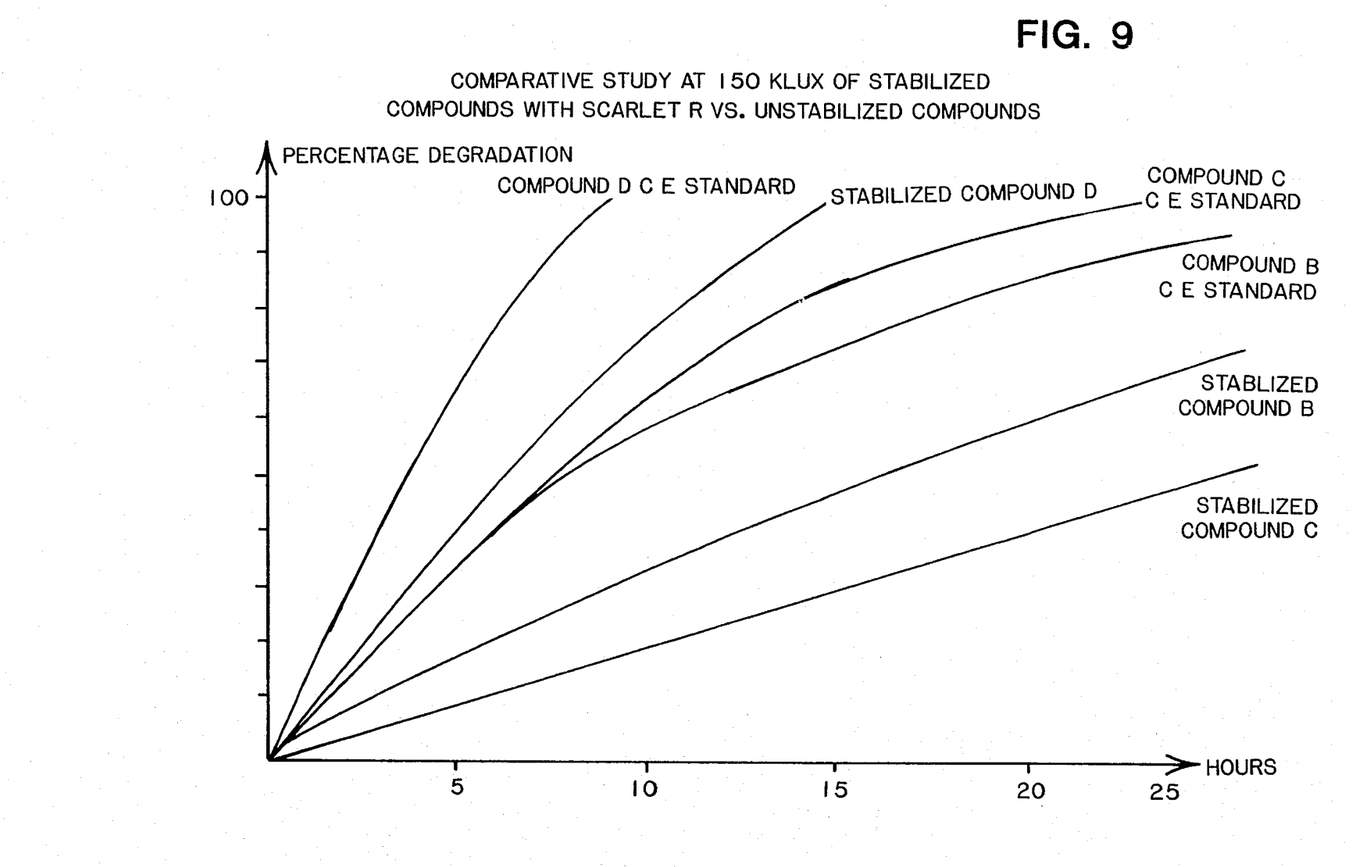
Figure 10:
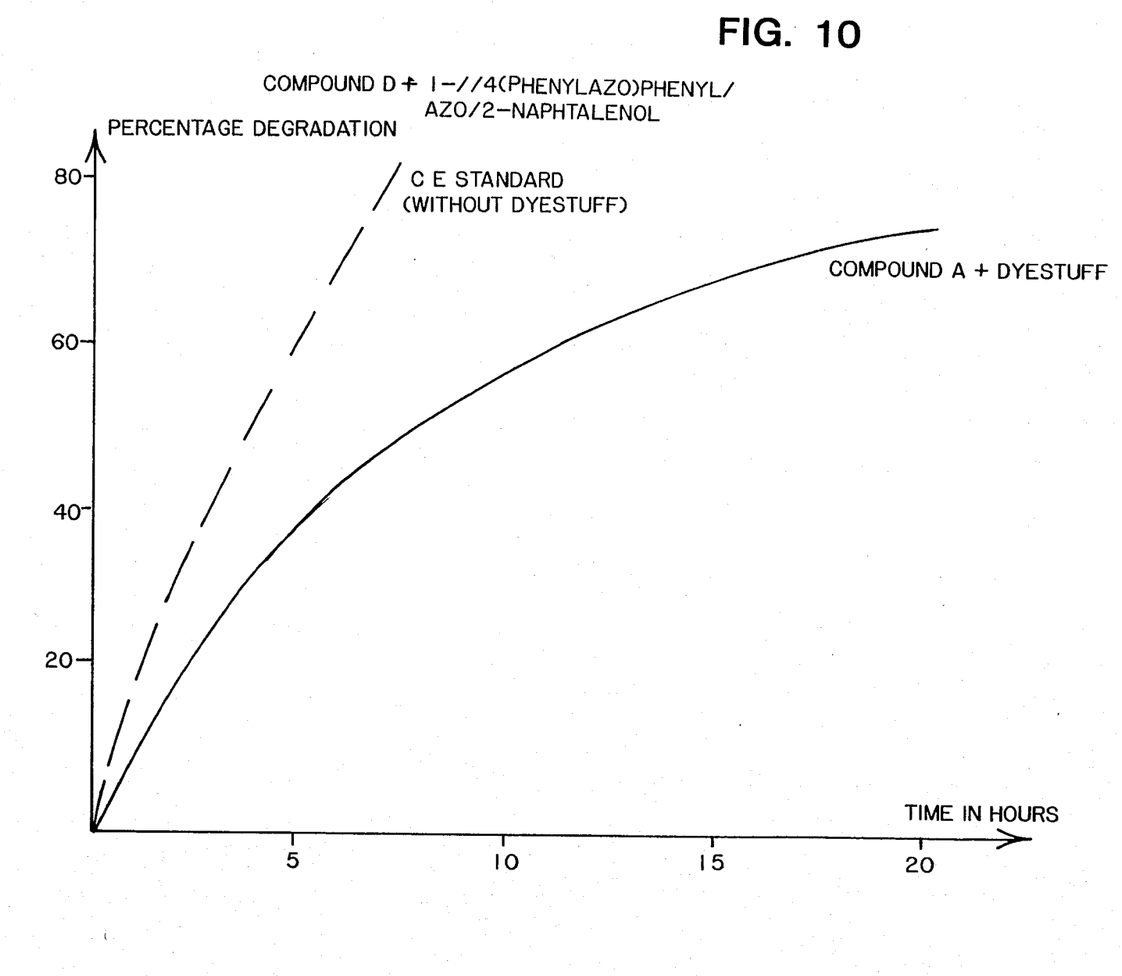

In the following examples there are described several preferred embodiments to illustrate the invention. However, it should be understood that the invention is not intended to be limited to the specific embodiments.

EXAMPLE 1

A stabilized composition was prepared consisting of 25 g of (S)α-cyano-3-phenoxy-benzyl (1R, cis) 2,2-dimethyl-3-(2,2-dibromovinyl)-cyclopropane-1-carboxylate, 70 g of non-ionic monolaurate of anhydrous sorbitol oxyethylene, 23 g of anionic sodium alkylnaphthalene sulfonate, 15 g of ethyl cellulose, 1 g of N,N-diethyl-4-(phenylazo)-benzeneamine (Yellow to fat GGN) and sufficient xylene for a total volume of one liter.

EXAMPLE 2

A stabilized composition was prepared consisting of 20 g of (S)α-cyano-3-phenoxy-benzyl (1R, trans) 2,2-dimethyl-3-(2,2-dichloro-1,2-dibromoethyl)-cyclopropane-1-carboxylate, 75 g of oxyethylene nonylphenol, 18 g of anionic lignosulfonate, 8 g of ethylcellulose, 1 g of N-ethyl-1-[{4-(phenylazo)phenyl}-azo]2-naphthalenylamine (Red to fat 7B) and sufficient toluene for a final volume of one liter.

STABILITY TEST

To determine the stability as a function of time, emulsifiable concentrates were prepared containing 25 g of the test pyrethrinoid compound, 82 g of a non-ionic oxyethylenated product of a mixture of aliphatic alcohols of 12 to 13 carbon atoms, 18 g of anionic calcium phenylsulfonate, 10 g of ethylcellulose, 1 g of azodyestuff and sufficient xylene for a final volume of one liter. The test compounds of formula I used were (S)α-cyano-3-phenoxy-benzyl (1R, cis) 2,2-dimethyl-3-(2,2-dibromovinyl)-cyclopropane-1-carboxylate [compound A], (S)α-cyano-3-phenoxy-benzyl (1R, cis) 2,2-dimethyl-3-(2,2-dichloro-1,2-dibromoethyl)-cyclopropane-1-carboxylate [compound B], (S)α-cyano-3-phenoxy-benzyl (1R, trans) 2,2-dimethyl-3-(2,2-dichloro-1,2-dibromoethyl)-cyclopropane-1-carboxylate [compound C] and (S)α-cyano-3-phenoxy-benzyl (1R, cis) 2,2-dimethyl-3-(1,2,2,2-tetrabromoethyl)-cyclopropane-1-carboxylate [compound D].

The test procedure involved measuring the kinetics of degradation under an overhead light by placing 200 μl of emulsifiable concentrate containing the active ingredient at a dose of 25 g/l (or 5 mg) in a beaker of 25 ml with a diameter of 30 mm so as to spread the deposit in the form of a ring on the bottom of the beaker. The test thus avoids surface irregularities in irradiation of the different samples. The organic solvent in the formulation was then removed by a current of hot air over about 20 minutes and the resulting beakers were then placed under an overhead light source (one hour of exposition at 150 klux = to 14 hours of average daylight) and held there for the indicated time. After light irradiation, the contents of the beaker were taken up in 1 to 2 ml of methylene chloride and the amount of the pyrethrinoid compounds was determined by high pressure liquid chromatography.

The mixtures of the test compound and azodyestuff used were (1) a mixture of compound A and N-ethyl-1-[{4-phenyl azo)-phenyl}-azo]-2-naphthalenylamine (Red to fat 7B), (2) a mixture of compound A and N,N-diethyl-4-(phenylazo)-benzeneamine (Yellow to fat GGN), (3) a mixture of compound B and red to fat 7B, (4) a mixture of compound B and Yellow to fat GGN, (5) a mixture of compound B and Ruby R (mixture of 1-[{-4-(phenylazo)-phenyl}-azo]-3-naphthalenol and 4-[{-4-(phenylazo)-phenyl}-azo]-phenol, (6) a mixture of compound C and red to fat 7B, (7) a mixture of compound C and red to fat GGN, (8) a mixture of compound C and Scarlet R, (9) a mixture of compound D and liquid red to fat 7B (a 65% solution of red to fat 7B in an aromatic solvent), (10) a mixture of compound D and blue to fat B or N-[4-(phenyl-{4-phenylamino}-1-naphthalenyl)-methylene]-2,5-cyclohexadien-1-ylidene-N-methyl-methaniminium chloride, (11) a mixture of compound D and liquid yellow to fat G (a liquid dye who structure is not indicated in Color Index), (12) a mixture of compound D and yellow to fat GGN, (13) a mixture of compound D and yellow to fat 3G or 2,4-dihydro-5-methyl-2-phenyl-4-phenylazo-3H-pyrazol-3-one, (14) a mixture of compound D and black to fat HB or 2,3-dihydro-2,2-dimethyl-6-[(4-phenylazo)-1-naphthalenyl]-azo-1H-perimidine, (15) a mixture of compound D powdered red to fat 7B, (16) a mixture of compound D and Scarlet R, (17) a mixture of compound D and red organol BS, (18) a mixture of compound D and red Sudan IV, (19) a mixture of compound D and vermillon organol, (20) a mixture of compound D and red to fat G, (21) a mixture of compound D and azo ruby, (22) a mixture of compound D and a mixture of ⅓ brown to fat B, ⅓ brown to fat RR and ⅓ Ruby RR to fat, (23) a mixture of compound D and brown to fat B, (24) a mixture of compound D and red to fat 5B, (25) a mixture of compound D and red to fat 7B, (26) a mixture of compound D and brown to fat RR, (27) a mixture of compound D and Red Sudan I, (28) a mixture of compound D and red Sudan II and (29) a mixture of compound D and 1-[{4-(phenylazo)-phenyl}-azo]-2-naphthalenol.

The results of the tests are expressed in the Figures submitted herewith wherein the percentage of degradation is plotted as a function of time. The tests were effected in comparison with a non-stabilized emulsifiable concentrate indicated as standard emulsifiable concentrate which was identical to the test compositions except for the presence of the azodyestuff.

Various modifications of the compositions and method of the invention may be made without departing from the spirit or scope thereof and it is to be understood that the invention is intended to be limited only as defined in the appended claims.

What is claimed is:

1. A light stable pyrethrinoid composition comprising (a) at least one liquid vehicle, (b) at least one surface-active agent soluble in the said liquid vehicle, (c) 0.1 to 10 gl/l of at least one azodyestuff stabilizer selected from the group consisting of N-ethyl-1-[{4-(phenylazo)-phenyl}-azo]-2-naphthalenylamine (Red to fat 7B), 1-[{1-naphthalenyl}-azo]-2,4-benzene-diamine (Brown RR to fat) and N,N-diethyl-4-(phenyl azo)-benzeneamine (Yellow to fat GGN), and (d) 5 to 100 g/l of at least one ester of the formula wherein Y is selected from the group consisting of in its various stereoisomeric forms and mixtures thereof, Z is alkyl of 1 to 6 carbon atoms, Y' is selected from the group consisting of hydrogen, halogen, —CN, —NO₃, alkyl of 1 to 4 carbon atoms and alkoxy of 1 to 4 carbon atoms, n is 0,1,2 or 3, W is selected from the group consisting of $X_1$ and $X_2$ are individually selected from the group consisting of fluorine, chlorine and bromine, $X_3$ is selected from the group consisting of chlorine, bromine and iodine, $X_4$ is a halogen and $X_5$ is a halogen other than that of $X_4$ and due to asymetric carbon atom in W, the compounds are in the A isomer or B isomer form or mixtures thereof and R is selected from the group consisting of and benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy, benzyl and halogens, $R_1$ is selected from the group consisting of hydrogen and methyl, $R_2$ is selected from the group consisting of monocyclic aryl and $-CH_2-C\equiv CH$, $R_3$ is an aliphatic of 2 to 6 carbon atoms having at least one carbon-carbon unsaturation, $R_4$ is selected from the group consisting of H, $-CN$, $-CH_3$ and $-C\equiv CH$, $R_5$ is selected from the group consisting of chlorine and methyl, n is 0, 1 or 2, $R_6$, $R_7$, $R_8$ and $R_9$ are individually selected from the group consisting of hydrogen, chlorine and methyl and S/I indicates that the ring may be aromatic, dihydro or tetrahydro, the alcoholic moiety R-OH being capable of containing one or more asymmetric carbon atoms and of existing in the form of various stereoisomers.

2. A composition of claim 1 in the form of an emulsifiable concentrate.

3. A composition of claim 1 wherein the azodyestuff is N-ethyl 1-[{4-(phenylazo)-phenyl}-azo]-2-naphthalenylamine.

4. A composition of claim 1 wherein the azodyestuff is N,N-diethyl-4-(phenylazo)-benzeneamine.

5. A composition of claim 1 wherein R is

6. A composition of claim 5 wherein R is selected from the group consisting of 3-phenoxy-benzyl, α-cyano-3-phenoxy-benzyl and α-ethynyl-3-phenoxy-benzyl.

7. A composition of claim 1 wherein the pyrethrinoid is (S)α-cyano-3-phenoxy-benzyl (1R, cis) 2,2-dimethyl-3-(2,2-dibromovinyl)-cyclopropane-1-carboxylate.

8. A composition of claim 1 wherein the pyrethrinoid is (S)α-cyano-3-phenoxy-benzyl (1R, cis) 2,2-dimethyl-3(2,2-dichloro-1,2-dibromoethyl)-cyclopropane-1-carboxylate.

9. A composition of claim 1 wherein the pyrethrinoid is (S)α-cyano-3-phenoxy-benzyl (1R, trans) 2,2-dimethyl-3-(2,2-dichloro-1,2-dibromoethyl)-cyclopropane-1-carboxylate.

10. A composition of claim 1 wherein the pyrethrinoid is (S)α-cyano-3-phenoxy-benzyl (1R, cis) 2,2-dimethyl-3-(1,2,2,2-tetrabromoethyl)-cyclopropane-1-carboxylate.

11. A composition of claim 1 wherein the surface active agent is selected from the group consisting of polyoxyethylene polymethylsiloxane, polyethylenepolyoxypropylene, polymethylsiloxane, monolaurate of sorbitol anhydrous oxyethylene, monooleate of sorbitol anhydrous oxyethylene, tridecyl alcohol oxyethylene, nonylphenol oxyethylene, polyglycolic ethers of fatty alcohols, tributylphenylpolyglycolic ethers, calcium salts of alkyl sulfonic acids and aryl sulfonic acids, phosphoric esters, alkylamino polycarboxylic acid derivatives, alkali metal salts of polyvalent amines, or organic carboxylic acids and organosulfonic acids, lignosulfonates, N-sulfo or N-phosphosuccinates of esters of amino acids, sodium alkylnaphthalene sulfonates, condensation products of aminosulfonic acids or aminocarboxylic acids with alkylhaloacetic acids and polyglycerol oleates.

12. A composition of claim 11 wherein the surface active agent is selected from the group consisting of oleates of polyglycerol and phosphoric acid esters.

13. A method of combatting pests comprising contacting pests with a pesticidal amount of a composition of claim 1.

14. A method of claim 13 wherein the composition is in the form of an emulsifiable concentrate.

15. A method of claim 13 wherein the azodyestuff is N-ethyl 1-[{4-(phenylazo)-phenyl}-azo]-2-naphthalenylamine.

16. A method of claim 13 wherein the azodyestuff is N,N-diethyl-4-(phenylazo)-benzeneamine.

17. A method of claim 13 wherein R is

18. A method of claim 13 wherein R is selected from the group consisting of 3-phenoxy-benzyl, α-cyano-3-phenoxybenzyl and α-ethynyl-3-phenoxy-benzyl.

19. A method of claim 13 wherein the pyrethrinoid is (S)α-cyano-3-phenoxy-benzyl (1R, cis) 2,2-dimethyl-3-(2,2-dibromovinyl)-cyclopropane-1-carboxylate.

20. A method of claim 13 wherein the pyrethrinoid is (S)α-cyano-3-phenoxy-benzyl (1R, cis) 2,2-dimethyl-3-(2,2-dichloro-1,2-dibromoethyl)-cyclopropane-carboxylate.

21. A method of claim 13 wherein the pyrethrinoid is (S)α-cyano-3-phenoxy-benzyl (1R, trans) 2,2-dimethyl-3-(2,2-dichloro-1,2-dibromoethyl)-cyclopropane-1-carboxylate.

22. A method of claim 13 wherein the pyrethrinoid is (S)α-cyano-3-phenoxy-benzyl (1R, cis) 2,2-dimethyl-3-(1,2,2,2-tetrabromoethyl)-cyclopropane-1-carboxylate.

23. A method of claim 13 containing 5 to 100 g per liter of the pyrethrinoid and 0.1 to 10 g per liter of azodyestuff.

24. A method of claim 13 wherein the surface active agent is selected from the group consisting of polyoxyethylene polymethylsiloxane, polyethylenepolyoxypropylene polymethyl silioxane, monolaurate of sorbitol anhydrous oxyethylene, monooleate of sorbitol anhydrous oxyethylene, tridecyl alcohol oxyethylene, nonylphenol oxyethylene, polyglycolic ether of fatty alcohols, tributylphenylpolycolic ethers, calcium salts of alkylsulfonic acids and arylsulfonic acids, phosphoric esters, alkylamines polycarboxylic acid, derivatives, alkali metal salts of polyvalent amines of organic carboxylic acids and organosulfonic acids, lignosulfonates, N-sulfo- or N-phosphosuccinates of esters of amino acids, sodium alkyl naphalene sulfonates, condensation products of aminosulfonic acids or aminocarboxylic acids with alkylhaloacetic acids and polyglycerol oleates.

25. A method of claim 13 wherein the surface active agent is selected from the group consisting of oleates of polyglycerol and phosphoric acid esters.

26. A process for stabilizing a liquid composition containing a light sensitive pyrethrinoid compound of claim 1 comprising incorporating therein at least one surface active agent soluble in the liquid media and at least one azodyestuff of claim 1.

27. A process of claim 26 wherein the composition contains 5 to 100 g per liter of the pyrethrinoid compound and 0.1 to 10 g per liter of the azodyestuff and 1 to 100 g/liter of surface active agent.

28. A process of claim 26 wherein the azodyestuff is N-ethyl 1-[{4-(phenylazo)-phenyl}-azo]-2-naphthalenylamine.

29. The method of claim 26 wherein the azodyestuff is N,N-diethyl-4-(phenylazo)-benzeneamine.

* * * * *